(12) United States Patent
Nalesnik

(10) Patent No.: US 7,704,929 B2
(45) Date of Patent: Apr. 27, 2010

(54) DIAROMATIC AMINE DERIVATIVES AS ANTIOXIDANTS

(75) Inventor: Theodore E. Nalesnik, Hopewell Junction, NY (US)

(73) Assignee: Chemtura Corporation, Middlebury, CT (US)

( * ) Notice: Subject to any disclaimer, the term of this patent is extended or adjusted under 35 U.S.C. 154(b) by 1142 days.

(21) Appl. No.: 11/326,165

(22) Filed: Jan. 4, 2006

(65) Prior Publication Data

US 2007/0155633 A1 Jul. 5, 2007

(51) Int. Cl.
*C10M 133/48* (2006.01)
*C07D 263/04* (2006.01)

(52) U.S. Cl. .................................. 508/270; 548/215

(58) Field of Classification Search ............... 548/215; 508/110, 243, 268, 269, 270
See application file for complete search history.

(56) References Cited

U.S. PATENT DOCUMENTS

| | | | |
|---|---|---|---|
| 3,293,181 A | 12/1966 | Stuart | |
| 3,396,109 A | 8/1968 | Butler et al. | |
| 3,397,145 A | 8/1968 | Cyba | |
| 3,442,804 A | 5/1969 | Le Suer et al. | |
| 3,507,880 A | 4/1970 | Altwicker | |
| 3,637,499 A | 1/1972 | Pollak | |
| 5,232,614 A | 8/1993 | Colclough et al. | |
| 5,498,809 A | 3/1996 | Emert et al. | |

FOREIGN PATENT DOCUMENTS

FR 1436583 4/1966

OTHER PUBLICATIONS

Lien, Eric J. Quantitative Structure-Activity Relationship Analysis of Phenolic Antioxidants. Free Radical Biology and Medicine. 26(3/4) (1999) 285-294.*
"International Preliminary Report on Patentability"; PCT/US2006/047454; Jul. 8, 2008; 5 Pages.

* cited by examiner

*Primary Examiner*—Kamal A Saeed
*Assistant Examiner*—Samantha L Shterengarts
(74) *Attorney, Agent, or Firm*—Katten Muchin Rosenman LLP

(57) ABSTRACT

Diraromatic amine derivatives having the general formula:

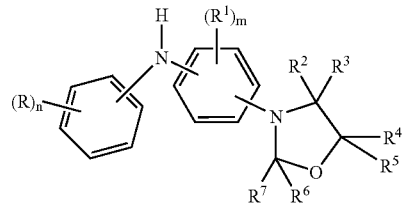

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing a functional group are provided. Also provided are lubricating oil compositions containing the diraromatic amine derivatives.

44 Claims, No Drawings

DIAROMATIC AMINE DERIVATIVES AS ANTIOXIDANTS

BACKGROUND OF THE INVENTION

1. Technical Field

The present invention generally relates to additives for stabilizing organic products that are subjected to oxidative, thermal, and/or light-induced degradation. More particularly, the present invention relates to a class of diaromatic amine derivatives useful as antioxidants.

2. Description of the Related Art

The stabilization of organic materials with antioxidants or other stabilizers are well known to those skilled in the art. For example, in developing lubricating oils, there have been many attempts to provide additives that impart, for example, antioxidant, antiwear, and deposit control properties thereto. Zinc dialkyldithiophosphates (ZDDP) have been used as antifatigue, antiwear, antioxidant, extreme pressure and friction modifying additives for lubricating oils for many years. However, they are subject to several drawbacks owing to their zinc and phosphorus contents. The presence of zinc contributes to the emission of particulates in the exhaust. In addition, during operation of an internal combustion engine, lubricating oil enters the combustion chambers by means such as clinging to cylinder walls as the piston makes its down stroke.

When phosphorus-containing lubricating oil compositions enter the combustion reaction, phosphorus enters the exhaust stream where it acts as a catalyst poison thus shortening the useful life of the catalytic converter. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and environmental reasons, but it is also important to maintain undiminished the antioxidant properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts.

It would therefore be desirable to provide improved additives for stabilizing organic products that are subject to oxidative, thermal, and/or light-induced degradation and in need of stabilization to prevent or inhibit such degradation, e.g., additives for lubricating oils that can improve the antioxidant properties of the oil while reducing the content of zinc and phosphorous of the lubricating oils.

SUMMARY OF THE INVENTION

In accordance with one embodiment of the present invention, a diaromatic amine derivative is provided having the general formula:

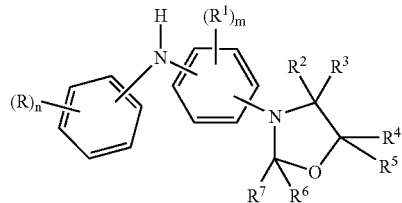

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing a functional group.

In accordance with a second embodiment of the present invention, a process for preparing a diaromatic amine derivative is provided, the diaromatic amine derivatives having the general formula:

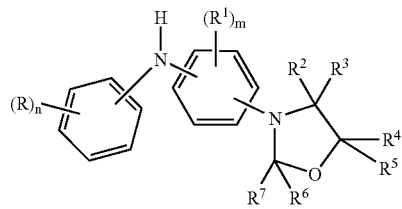

wherein n, m, R, $R^1$, $R^2$, $R^3$, $R^4$, $R^5$, $R^6$ and $R^7$ have the aforementioned meanings, the process comprising reacting a hydroxyl ethylene amine intermediate of the formula

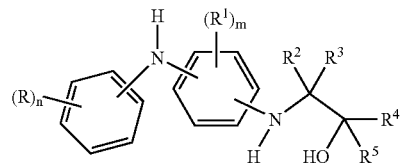

wherein n, m, R, $R^1$, $R^2$, $R^3$, $R^4$ and $R^5$ have the aforementioned meanings, with a ketone or aldehyde.

In accordance with a third embodiment of the present invention, a process for preparing one or more diaromatic amine derivatives is provided, the one or more diaromatic amine derivatives having the general formula:

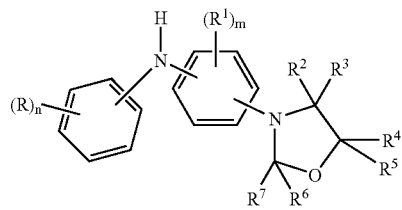

wherein n, m, R, $R^1$, $R^2$, $R^3$, $R^4$, $R^5$, $R^6$ and $R^7$ have the aforementioned meanings, the process comprising (a) reacting a substituted or unsubstituted N-phenyl-p-phenylenediamine derivative with an organic epoxide radical; and (b) reacting the product of step (a) with a ketone or aldehyde.

In accordance with a fourth embodiment of the present invention, a lubricating oil composition is provided comprising (a) an oil of lubricating viscosity and (b) an antioxidant improving effective amount of one or more of the foregoing diaromatic amine derivatives.

In accordance with a fifth embodiment of the present invention, a stabilizer-containing composition is provided comprising (a) an organic material subject to oxidative, thermal, and/or light-induced degradation and in need of stabilization to prevent or inhibit such degradation; and (b) a stabilizing effective amount of one or more of the foregoing diaromatic amine derivatives.

In accordance with a sixth embodiment of the present invention a method for stabilizing an organic material subject to oxidative, thermal, and/or light-induced degradation and in need of stabilization to prevent or inhibit such degradation is provided, the method comprising adding to the organic material a stabilizing effective amount of one or more of the foregoing diaromatic amine derivatives.

The present invention advantageously provides diaromatic amine derivative additives and lubricating oil compositions which provide deposit protection in addition to oxidation-corrosion protection. The lubricating oil compositions can also provide such protection while having only low levels of phosphorous, i.e., less than about 0.1%, preferably less than about 0.08% and more preferably less than about 0.05% by weight. Accordingly, the lubricating oil compositions of the present invention can be more environmentally desirable than the higher phosphorous lubricating oil compositions generally used in internal combustion engines because they facilitate longer catalytic converter life and activity while also providing the desired high deposit protection. This may be due to the substantial absence of additives containing phosphorus compounds in these lubricating oil compositions. The diaromatic amine derivative additives of this invention may also protects against oxidation both in the presence of transition metals such as, for example, iron (Fe) and Copper (Cu) etc. as well as in a metal free environment.

DETAILED DESCRIPTION OF THE PREFERRED EMBODIMENTS

The diaromatic amine derivatives, useful as antioxidants, of the present invention are represented by the general formula:

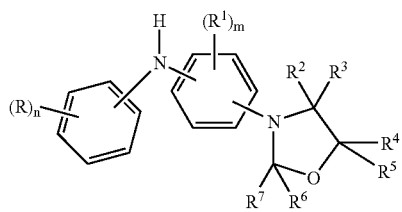

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, e.g., N, S or O, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing a functional group, e.g., an ester group, an ether group, an aromatic group or an amide group.

Generally, the diaromatic amine derivatives of the present invention can be obtained by reacting a beta hydroxyl ethylene amine intermediate of the general formula:

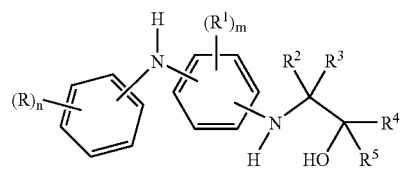

wherein n, m, R, $R^1$, $R^2$, $R^3$, $R^4$ and $R^5$ have the aforementioned meanings with a ketone or aldehyde. Generally, the hydroxyl ethylene amine intermediate can be prepared by reacting a substituted or unsubstituted N-phenyl-p-phenylenediamine derivative with an organic epoxide radical.

A substituted or unsubstituted N-phenyl-p-phenylenediamine derivative for use in forming the hydroxyl ethylene amine, intermediate can be represented by the formula:

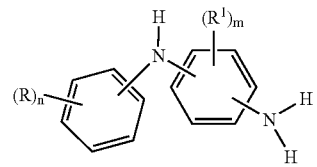

wherein n, m, R and $R^1$ have the aforementioned meanings. Representative examples of the suitable substituted or unsubstituted N-phenyl-p-phenylenediamine derivatives include, but are not limited to, p-N-phenylphenylenediamine, N-phenyl-o-phenylenediamine, N-naphthyl-p-phenylenediamine, N-naphthyl-o-phenylenediamine, N-(5,6,7,8-tetrahydro-1-naphthyl)-p-phenylenediamine, N-(5,6,7,8-tetrahydro-2-naphthyl)-p-phenylenediamine, N-(5,6,7,8-tetrahydro-1-naphthyl)-o-phenylenediamine, N-(5,6,7,8-tetrahydro-2-naphthyl)-o-phenylenediamine, and the like and combinations thereof. Preferably, the N-phenyl-p-phenylenediamine is N-p-phenylphenylenediamine.

Suitable organic epoxide radicals include, but are not limited to, epoxidized hydrocarbon olefins, epoxidized vinyl ethers, epoxidized vegetable oils, epoxidized unsaturated fatty esters of vegetable oils, 1,2-epoxyalkyl or 1,2-epoxycycloalkyl and the like and mixtures thereof. As one skilled in the art will readily appreciate, by reacting an unsymmetrical epoxide radical with any N-phenyl-phenylenediamine derivative will result in a mixture of two isomers depending on which side of the epoxide radical is nucleophilically attacked by the N-phenyl-phenylenediamine derivative. Representative examples of suitable organic epoxide groups for use herein include, but are not limited to, epoxycyclohexane, 1,2-epoxynonane, 1,2-epoxydecane, 1,2-epoxydodecane, 1,2-epoxytetradecane, 1,2-epoxyhexadecane, 1,2-epoxyoctadecane, 2-ethylhexyl glycidol ether, hexyl glycidol ether, butyl glycidol ether, heptyl glycidol ether, octyl glycidol ether, nonyl glycidol ether, decyl glycidol ether, undecyl glycidol ether, dodecyl glycidol ether, tetra glycidol ether, hexadecyl glycidol ether, octadecyl glycidol ether, octadecenyl glycidol ether, epoxy methyl oleate, epoxy 2-ethylhexyl oleate, epoxy butyl oleate, epoxy methyl docesenate and epoxides of all other fatty acid esters of all unsaturated vegetable oils and the like and mixtures thereof.

The substituted or unsubstituted N-phenyl-p-phenylenediamine derivatives and organic epoxide radicals are advantageously reacted to form the hydroxyl ethylene amine intermediate in a mole ratio ordinarily ranging from about 0.9:1 to about 1:1 and preferably about 1:1 of organic epoxide radical to N-phenyl-p-phenylenediamine. The reaction is ordinarily conducted at a temperature ranging from about 30° C. to about 150° C. and preferably from about 50° C. to about 100° C. The time for preparing the hydroxyl ethylene amine intermediate, under preferred parameters, will generally not exceed about 10 hours.

If desired, the reaction of the substituted or unsubstituted N-phenyl-p-phenylenediamine derivatives and organic epoxide radicals can be carried out in a suitable solvent. A suitable solvent used in this step should be one that will not itself react with the epoxide radical. Examples of such solvents include, but are not limited to, aliphatic and aromatic hydrocarbons; e.g., hexanes, cyclohexane, benzene, toluene and xylenes; ethers, e.g., dioxanes and dialkyl glycol ethers, and the like and mixtures thereof. The reaction can also be carried out in the presence of a suitable catalyst. A suitable catalyst can include acid catalysts such as, for example, acid clay catalysts; organic sulfonate acids, e.g., toluenesulfonic acid and methanesulfonic acid; Lewis acids, e.g., $BCl_3$, $BF_3$, and $AlCl_3$; zeolite catalysts and the like and mixtures thereof.

The hydroxyl ethylene amine intermediate is then reacted with a ketone or aldehyde to provide the diaromatic amine derivatives of this invention. Suitable ketones include, but are not limited to, acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone), 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-neptanone, 5,6-dimethyl-4-heptanone, 6,6-dimethyl-4-heptanone, 2-undecanone, cyclohexanone, cycloheptanone, and the like and combinations thereof.

Suitable aldehydes include, but are not limited to, formaldehyde, acetaldehyde, propionaldehyde, butyraldehyde, 2-methylpropionaldehyde, valeraldehyde, 2-methyl-butanal, caproaldehyde, hexaldehyde, heptaldehyde, octaldehyde, nonaldehyde, decaldehyde, undecaldehyde, dodecaldehyde, benzaldehyde, phenylacetaldehyde, and the like and combinations thereof. A preferred aldehyde for use herein is formaldehyde.

The reaction of the beta hydroxyl ethylene amine intermediate with a ketone or aldehyde can be carried out in the same solvent used in the first step or a different solvent with or without an acid catalyst to form the diaromatic amine derivative final product. When using a suitable solvent, the water by-product can be removed azeotropically. The acid catalyst, if present, can be extracted or removed and the solvent stripped off. The final product may contain some small amounts of unreacted intermediate and methylated product with methylation on the secondary di-phenylamine nitrogen. This can be observed when formaldehyde is used as the cyclization aldehyde. These materials may also be expected to also have antioxidant performance properties if present.

Generally, the hydroxyl ethylene amine intermediate and ketone or aldehyde are advantageously reacted to provide a product mixture containing at least one diaromatic amine derivative. If desired, the derivatives can be isolated using conventional techniques, e.g., chromatography. The amount of ketone or aldehyde reacted with the hydroxyl ethylene amine intermediate will range from about 0.95 equivalents to about 1.4 equivalents of ketone or aldehyde to hydroxyl ethylene amine intermediate and preferably from about 1.0 equivalents to about 1.1 equivalents of ketone or aldehyde to hydroxyl ethylene amine intermediate. The temperature of this reaction will ordinarily range from about 25° C. to about 110° C. and preferably from about 60° C. to about 100° C.

The diaromatic amine derivatives of this invention may have useful antioxidant properties for use as antioxidants in, for example, compounded tires, polyols, plastics, urethanes, greases, motor oils, rubber belts, cables, gaskets, seals, rubber products in the garment and carpet industries. Accordingly, an embodiment of the present invention is a stabilizer-containing composition containing an organic material subject to oxidative, thermal, and/or light-induced degradation and in need of stabilization to prevent or inhibit such degradation and, as a stabilizer therefore, the foregoing diaromatic amine derivatives. The diaromatic amine derivative stabilizer can be added to the organic material in an amount sufficient to impart an appreciable stabilizing effect. In general, this amount may vary from about 0.1 wt. % to about 5 wt. % weight percent, preferably from about 0.5 wt. % to about 3 wt. % weight percent and more preferably from about 0.5 wt. % to about 2 wt. % by total weight of the organic material.

Another embodiment of the present invention is a lubricating oil composition containing at least (a) an oil of lubricating viscosity and (b) an effective amount of at least one of the foregoing diaromatic amine derivatives. Generally, the oil of lubricating viscosity for use in the lubricating oil compositions may be present in a major amount, e.g., an amount of greater than about 50 wt. %, preferably greater than about 70 wt. %, more preferably from about 80 to about 99.5 wt. % and most preferably from about 85 to about 98 wt. %, based on the total weight of the composition. The oil of lubricating viscosity for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, e.g., automatic transmission fluids, etc., turbine lubricants, compressor lubricants, metal-working lubricants, and other lubricating oil and grease compositions. Additionally, the oil of lubricating viscosity for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the oil of lubricating viscosity is dependent upon the application. Accordingly, the viscosity of an oil of lubricating viscosity for use herein will ordinarily range from about 2 to about 2000 centistokes (cSt) at 100° Centigrade (C.). Generally, individually the oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable oil of lubricating viscosity is one that comprises little, if any, heavy fraction; e.g., little, if any, lube oil fraction of viscosity about 20 cSt or higher at 100° C.

The oil of lubricating viscosity may be derived from natural lubricating oils, synthetic lubricating oils or mixtures thereof. Suitable oils includes base stocks obtained by isomerization of synthetic wax and slack wax, as well as hydrocracked base stocks produced by hydrocracking (rather than solvent extracting) the aromatic and polar components of the crude. Suitable oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of about 1,000, diphenyl ether of polyethylene glycol having a molecular weight of about 500 to about 1000, diethyl ether of polypropylene glycol having a molecular weight of about 1,000 to about 1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The oil of lubricating viscosity may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The diaromatic amine derivative additives of this invention can be used as a complete or partial replacement for commercially available antioxidants currently used in lubricant formulations and can be in combination with other additives typically found in motor oils and fuels. When used in combination with other types of antioxidants or additives used in oil formulations, synergistic and/or additive performance effects may also be obtained with respect to improved antioxidancy, antiwear, frictional, detergency and engine high temperature deposit properties. Such other additives can be any presently known or later-discovered additives used in formulating lubricating oil compositions. The lubricating oil additives typically found in lubricating oils are, for example, dispersants, detergents, corrosion/rust inhibitors, antioxidants, anti-wear agents, anti-foamants, friction modifiers, seal swell agents, emulsifiers, VI improvers, pour point depressants, and the like. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like. Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of other antioxidants include alkylated diphenylamines, N-alkylated phenylenediamines, phenyl-∀-naphthylamine, alkylated phenyl-∀-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like. The following are exemplary of such additives and are commercially available from Chemtura Corporation: Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard® BHT, Naugalube 403, and Naugalube 420, among others.

Examples of anti-wear additives that can be used in combination with the additives of the present invention include organo-borates, organo-phosphites, organo-phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like. Representative examples of such additives are those commercially available from The Lubrizol Corporation such as Lubrizol 677A, Lubrizol 1095, Lubrizol 1097, Lubrizol 1360, Lubrizol 1395, Lubrizol 5139, Lubrizol 5604 and the like, and from Ciba Corporation such as Irgalube 353 and the like.

Examples of friction modifiers include fatty acid esters and amides, organo molybdenum compounds, molybdenum dialkyldithiocarbamates, molybdenum dialkyl-dithiophosphates, molybdenum disulfide, tri-molybdenum cluster dialkyldithiocarbamates, non-sulfur molybdenum compounds and the like. Representative examples of such friction modifiers are those commercially available from R.T. Vanderbilt Company, Inc. such as Molyvan A, Molyvan L, Molyvan 807, Molyvan 856B, Molyvan 822, Molyvan 855, and the like; Asahi Denka Kogyo K.K. such as SAKURA-LUBE 100, SAKURA-LUBE 165, SAKURA-LUBE 300, SAKURA-LUBE 310G, SAKURA-LUBE 321, SAKURA-LUBE 474, SAKURA-LUBE 600, SAKURA-LUBE 700, and the like; and from Akzo Nobel Chemicals GmbH such as Ketjen-Ox 77M, Ketjen-Ox 77TS, and the like.

An example of an anti-foam agent is polysiloxane, and the like. Examples of rust inhibitors are polyoxyalkylene polyol, benzotriazole derivatives, and the like. Examples of VI improvers include olefin copolymers and dispersant olefin copolymers, and the like. An example of a pour point depressant is polymethacrylate, and the like.

As noted above, suitable anti-wear compounds include dihydrocarbyl dithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

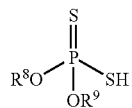

wherein $R^8$ and $R^9$ are the same or different and can be linear or branched alkyl, cycloalkyl, aralkyl, alkaryl, or substituted substantially hydrocarbyl radical derivatives of any of the above groups, and wherein the $R^8$ and $R^9$ groups in the acid each have, on average, at least 3 carbon atoms. By "substantially hydrocarbyl" is meant radicals containing substituent groups, e.g., 1 to 4 substituent groups per radical moiety such as, for example, ether, ester, thio, nitro, or halogen, that do not materially affect the hydrocarbon character of the radical.

Specific examples of suitable $R^8$ and $R^9$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, beta-octylbutyl-naphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having from about 3 to about 30 carbon atoms and aryl radicals having from about 6 to about 30 carbon atoms are preferred. Particularly preferred $R^8$ and $R^9$ radicals are alkyl of from 4 to about 18 carbon atoms.

The phosphorodithioic acids are readily obtainable by the reaction of a phosphorus pentasulfide and an aliphatic alcohol and/or phenol. The reaction involves at least mixing, at a temperature ranging from about 20° C. to 200° C., about 4 moles of the alcohol or phenol with one mole of phosphorus pentasulfide. Hydrogen sulfide can be liberated as the reaction takes place. Mixtures of alcohols, phenols, or both can be employed, e.g., mixtures of $C_3$ to $C_{30}$ alcohols, $C_6$ to $C_{30}$ aromatic alcohols, etc. The metals useful to make the phosphate salts include, but are not limited to, Group I metals, Group II metals, aluminum, lead, tin, molybdenum, manganese, cobalt, and nickel with zinc being the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate and the like and mixtures thereof.

In some instances, the incorporation of certain ingredients, particularly carboxylic acids or metal carboxylates, e.g., small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art. See, e.g., U.S. Pat. Nos. 3,293,181; 3,397,145; 3,396,109 and 3,442,804, the contents of which are hereby incorporated by reference. Also useful as antiwear additives are amine derivatives of dithiophosphoric acid compounds, such as are described in U.S. Pat. No. 3,637,499, the content of which is hereby incorporated by reference in its entirety.

The zinc salts are most commonly used as anti-wear additives in lubricating oils in amounts ranging from about 0.1 to about 10, preferably about 0.2 to about 2 wt. %, based upon the total weight of the lubricating oil composition. They may be prepared in accordance with known techniques, e.g., by first forming a dithiophosphoric acid, usually by reaction of an alcohol and/or a phenol with $P_2S_5$ and then neutralizing the dithiophosphoric acid with a suitable zinc compound.

Mixtures of alcohols can be used, including mixtures of primary and secondary alcohols, secondary generally for imparting improved antiwear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

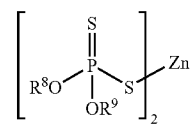

wherein $R^8$ and $R^9$ have the aforestated meanings.

The lubricating oil compositions of the present invention, when they contain these additives, are typically blended into a base oil in amounts such that the additives therein are effective to provide their normal attendant functions. Representative effective amounts of such additives are illustrated in Table 1.

TABLE 1

| Additives | Preferred Weight % | More Preferred Weight % |
|---|---|---|
| V.I. Improver | about 1 to about 12 | about 1 to about 4 |
| Corrosion Inhibitor | about 0.01 to about 3 | about 0.01 to about 1.5 |
| Oxidation Inhibitor | about 0.01 to about 5 | about 0.01 to about 1.5 |
| Dispersant | about 0.1 to about 10 | about 0.1 to about 5 |
| Lube Oil Flow Improver | about 0.01 to about 2 | about 0.01 to about 1.5 |
| Detergent/Rust Inhibitor | about 0.01 to about 6 | about 0.01 to about 3 |
| Pour Point Depressant | about 0.01 to about 1.5 | about 0.01 to about 0.5 |
| Anti-foaming Agents | about 0.001 to about 0.1 | about 0.001 to about 0.01 |
| Anti-wear Agents | about 0.001 to about 5 | about 0.001 to about 1.5 |
| Seal Swell Agents | about 0.1 to about 8 | about 0.1 to about 4 |
| Friction Modifiers | about 0.01 to about 3 | about 0.01 to about 1.5 |
| Lubricating Base Oil | Balance | Balance |

When other additives are employed, it may be desirable, although not necessary, to prepare additive concentrates comprising concentrated solutions or dispersions of the diaromatic amine derivative additives of this invention (in concentrate amounts hereinabove described), together with one or more other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by, for example, solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to about 20 weight percent of the additive package with the remainder being base oil.

All of the weight percentages expressed herein (unless otherwise indicated) are based on the active ingredient (AI) content of the additive, and/or upon the total weight of any additive package, or formulation, which will be the sum of the AI weight of each additive plus the weight of total oil or diluent.

In general, the lubricating oil compositions of the present invention can contain the additives in a concentration ranging from about 0.05 to about 30 weight percent, preferably from about 0.1 to about 10 weight percent, and preferably from about 0.2 to about 5 weight percent, based on the total weight of the oil composition. In one embodiment, oil concentrates of the additives can contain from about 1 to about 75 weight percent of the additive in a carrier or diluent oil of lubricating oil viscosity.

The following non-limiting examples are illustrative of the present invention.

Preparation of Additives

Example 1

Preparation of a mixture of 5-decyl-N—(N'-p-phenylanilino)-1,3-oxazolidine and 4-decyl-N—(N'-p-phenylanilino)-1,3-oxazolidine Into a 250 ml reaction flask was charged 60 g (0.32 mol) of p-N-phenylphenylenediamine, 62 g (0.32 mol) of 1,2-epoxydodecane, 75 ml of cyclohexane and 6.0 g of an acid clay catalyst. The reaction mixture was stirred under a blanketed with argon and heated to 75° C. These reaction conditions were maintained for 4 hours. The reaction temperature was then lowered to 50° C. and the reaction mixture was filtered to remove the clay catalyst. The hot filtered reaction material was transferred to a 500 ml reaction flask equipped with a Deans-Stark water trap. The reaction media was stirred under argon blanket and heated to 60° C. followed by the 2.5 hour addition of 28 g (0.35 mol) of 37% formalin. After the formalin addition was complete, the temperature was maintained at 60° C. for one hour before raising the temperature to reflux to remove water to the Deans-Stark trap. After the water was removed, the temperature was held at 85° C. for one hour before reducing it to 50° C. The reaction media was now filtered and the solvent stripped off under vacuum. The final product (116 g) solidified on cool down to a gray-white paste.

Example 2

Preparation of a mixture of 5-dodecyl-N—(N'-p-phenylanilino)-1,3-oxazolidine and 4-dodecyl-N—(N'-p-phenylanilino)-1,3-oxazolidine Into a 100 ml reaction flask was charged 18.6 g (0.1 mol) of p-N-phenylphenylenediamine, 27.5 g (0.11 mol) of 1,2-epoxytetradecane, 25 ml of cyclohexane and 3.0 g of an acid clay catalyst. The reaction mixture was stirred under a blanketed with argon and heated to 75° C. These reaction conditions were maintained for 4 hours. The reaction temperature was then lowered to 60° C. and the reaction mixture was filtered to remove the clay catalyst. The hot filtered reaction material was transferred to a 100 ml reaction flask equipped with a Deans-Stark water trap. The reaction media was stirred under argon blanket and heated to 60° C. followed by the 1.5 hour addition of 10 g (0.12 mol) of 37% formalin. After the formalin addition was complete, the temperature was maintained at 60° C. for one hour before raising the temperature to reflux to remove water to the Deans-Stark trap. After the water was removed, the temperature was held at 85° C. for one hour before reducing it to 50° C. The reaction media was now filtered and the solvent stripped off under vacuum. The final product (43 g) solidified on cool down to a gray-white paste.

Example 3

Preparation of a mixture of 5-(2-ethylhexyl)oxymethylene-N—(N'-p-phenylanilino)-1,3-oxazolidine and 4-(2-ethylhexyl)oxymethylene-N—(N'-p-phenylanilino)-1,3-oxazolidine Into a 100 ml reaction flask was charged 18.6 g (0.1 mol) of p-N-phenylphenylenediamine, 19.5 g (0.11 mol) of 2-ethylhexyl glycidol ether, 25 ml of cyclohexane and 3.0 g of an acid clay catalyst. The reaction mixture was stirred under a blanketed with argon and heated to 75° C. These reaction conditions were maintained for 3 hours. The reaction temperature was then lowered to 60° C. and the reaction mixture was filtered to remove the clay catalyst. The hot filtered reaction material was transferred to a 100 ml reaction flask equipped with a Deans-Stark water trap. The reaction media was stirred under argon blanket and heated to 60° C. followed by the 1.5 hour addition of 9.0 g (0.11 mol) of 37% formalin. After the formalin addition was complete, the temperature was maintained at 60° C. for one hour before raising the temperature to reflux to remove water to the Deans-Stark trap. After the water was removed, the temperature was held at 105° C. for one hour before reducing it to 50° C. The reaction media was now filtered and the solvent stripped off under vacuum. The final product was a reddish-gray viscous liquid.

Preparation of SAE 10W-30 Motor Oil Formulations

Example 4

Preparation of SAE 10W-30 Motor Oil Formulation

The SAE 10W-30 motor oil formulation set forth in Table 2 was prepared with 1 weight percent of the additive of Example 1.

TABLE 2

| SAE 10W-30 Motor Oil Formulation (Base Blend) | |
|---|---|
| | Amount, wt. % |
| Overbased Calcium Sulfonate Detergent | 1.3 |
| Rust/Corrosion Inhibitor | 0.75 |
| Pour Point Depressant | 0.1 |
| OCP VI Improver | 5.5 |
| ZDDP | 0.8 |
| Solvent Neutral 100 | Balance |

Example 5

Preparation of SAE 10W-30 Motor Oil Formulation

The SAE 10W-30 motor oil formulation set forth in Table 2 was prepared with 1 weight percent of the additive of Example 2.

Example 6

Preparation of SAE 10W-30 Motor Oil Formulation

The SAE 10W-30 motor oil formulation set forth in Table 2 was prepared with 1 weight percent of the additive of Example 3.

Comparative Blend A

Preparation of SAE 10W-30 Motor Oil Formulation

The SAE 10W-30 motor oil formulation set forth in Table 2 was prepared with no antioxidant added of any type.

Preparation of Turbine Oil Formulations

Example 7

Preparation of a Turbine Oil Formulation

The turbine oil test formulation set forth in Table 3 was prepared with 1 weight percent of the additive of Example 1.

TABLE 3

| Turbine Reference Test Oil Composition | |
| --- | --- |
| Additive Component in Oil | Amount, wt. % in composition |
| Corrosion Inhibitor | 0.05 wt. % |
| Defoamer | 0.005 wt. % |
| Metal Deactivator | 0.03 wt. % |
| Exxon 100LP | Balance |

Example 8

Preparation of a Turbine Oil Formulation

The turbine oil test formulation set forth in Table 3 was prepared with 1 weight percent of the additive of Example 2.

Example 9

Preparation of a Turbine Oil Formulation

The turbine oil test formulation set forth in Table 3 was prepared with 1 weight percent of the additive of Example 3.

Comparative Blend B

Preparation of a Turbine Oil Formulation

The turbine oil test formulation set forth in Table 3 was prepared with no antioxidant added of any type.

Preparation of Pressure Differential Scanning Calorimetry (PDSC) Test Oils

Example 10

Preparation of a PDSC Multigrade Motor Oil Formulation

The motor oil formulation set forth in Table 4 prepared with 1 weight percent of the additive of Example 1. The components used in the engine oil formulation are commercially available. There is no particular restriction on the type and exact composition of the materials in the context of the present invention.

TABLE 4

| Composition | Amount, wt. % |
| --- | --- |
| Base oil, Solvent Neutral 150 | 83.85 |
| Zinc Dialkyldithiophosphonate | 1.01 |
| Succinimide Dispersant | 7.58 |
| Overbased Calcium sulfonate detergents | 1.31 |
| Neutral Calcium sulfonate detergents | 0.50 |
| Pour Point Depressant | 0.10 |
| Rust Inhibitor | 0.10 |
| VI improver | 5.55 |

Example 11

Preparation of a PDSC Multigrade Motor Oil Formulation

The motor oil formulation set forth in Table 4 prepared with 1 weight percent of the additive of Example 2.

Example 12

Preparation of a PDSC Multigrade Motor Oil Formulation

The motor oil formulation set forth in Table 4 prepared with 1 weight percent of the additive of Example 3.

Comparative Example C

Preparation of a PDSC Multigrade Motor Oil Formulation

The motor oil formulation set forth in Table 4 prepared with no antioxidant added of any type.

Testing

To demonstrate the effectiveness of the additives of Examples 1-3 of the present invention, each of the oil formulations of Examples 4-6 and Comparative Example A were evaluated using the Thermo-Oxidation Engine Oil Simulation Test (TEOST), each of the turbine oil formulations of Examples 7-9 and Comparative Example B were evaluated using the Rotary Bomb Oxidation Test (RBOT) and each of the PDSC multigrade motor oil formulations of Examples 10-12 and Comparative Example C were evaluated as described below.

Mid-High Temperature Thermo-Oxidative Engine Oil Simulation Test (TEOST)

The Mid-High Temperature Thermo-oxidative Engine Oil Simulation Test (MHT TEOST) was performed to determine the deposit forming tendencies of the motor engine oil. The improved thermal deposit control of the additives of this invention in stabilizing the engine oil formulation has been clearly demonstrated by the MHT TEOST. This test determines the mass of deposit formed on a specially constructed steel rod by continuously stressing a repetitive passage of 8.5 ml of test oil under thermal-oxidative and catalytic conditions. The instrument used was manufactured by Tannas Co. and has a typical repeatability of 0.15(x+16) mg wherein x is the mean of two or more repeated test results. The TEOST test conditions are listed in Table 5. The less the amount of deposits obtained, the better the oxidation stability of the oil.

TABLE 5

TEOST MHT Test Conditions

| Test Parameters | Settings |
| --- | --- |
| Test duration | 24 hours |
| Rod Temperature | 285° C. |
| Sample size | 8.5 g (mixture of 8.4 g of oil and 0.1 g of catalyst) |
| Sample flow rate | 0.25 g/min |
| Flow rate (dry air) | 10 mL/min |
| Catalyst | Oil soluble mixture containing Fe, Pb, and Sn |

The results of the TEOST are set forth in Table 6. The significantly lower amounts of deposits obtained from the blends of Examples 4-6 as compared to the blend of Comparative Example A containing no antioxidant, as shown in the data set forth in Table 6, demonstrate that the lubricating oil compositions containing the antioxidant of this invention have superior oxidative stability to produce smaller amounts of deposits in the TEOST.

TABLE 6

TEOST Results

| Ex./Comp. Ex. | mg deposits |
| --- | --- |
| Example 4 | 62 |
| Example 5 | 75 |
| Example 6 | 71 |
| Comp. Ex. A | 110 |

It can be seen from the above data that the addition of a diaromatic amine derivative additive of the present invention to a motor oil formulation significantly reduces the total deposit mass of the base blend formulation.

Rotary Bomb Oxidation Test (RBOT)

The Rotary Bomb Oxidation test (RBOT) was conducted according to the standard test method specified by ASTM D 2272-85. The time for a 25 psi pressure drop was 100 minutes for the Reference Oil. The longer the time to reach the endpoint indicates improved oxidative stability.

This test method utilizes an oxygen-pressured bomb to evaluate the oxidation stability of new and in service turbine oils having the same composition (base stock and additives) in the presence of water and a copper catalyst coil at 150° C. The test oil, water and a copper catalyst coil, contained in a covered glass container, are placed in a bomb equipped with a pressure gauge. The bomb is charged with oxygen to a pressure of 90 psi and placed in a constant temperature oil bath set at 150° C., and rotated axially at 100 rpm at an angle of 30 degrees from the horizontal. The number of minutes required to reach a specific drop in gage pressure (in this test for this invention, 25 psi) is the oxidation stability of the test sample. The RBOT conditions are given in Table 7

TABLE 7

RBOT Test Conditions

Initial Conditions

| Copper Catalyst Coil Weight | 55.6 grams |
| --- | --- |
| Sample Size Weight | 50.00 grams |
| Distilled Water weight | 5 grams |
| Temperature, C. | 150° C. |
| Oxygen Initial Pressure at RT | 90° C. |
| Oxygen Max Pressure at 150 C. | 188 psi |
| Pressure Drop to End Test | 25 psi |

The results of this test are set forth in Table 8.

TABLE 8

RBOT Results

| Ex./Comp. Ex. | Time, minutes |
| --- | --- |
| Example 7 | 578 |
| Example 8 | planned |
| Example 9 | planned |
| Comp. Ex. B | <100 |

It can be seen from the above data that the turbine oil formulations containing the diaromatic amine derivative additives of the present invention possessed significantly better oxidative stability than the turbine oil formulation of Comparative Example B which is outside the scope of the invention.

Pressurized Differential Scanning Calorimetry (PDSC)

The PDSC measures the oxidation induction time (OIT) of each blend. The PDSC instrument used is a Mettler DSC27HP manufactured by Mettler-Toledo, Inc (Switzerland). The PDSC method employs a steel cell under constant oxygen pressure throughout each run. The instrument has a typical repeatability of ±2.5 minutes with 95 percent confidence over an OIT of 100 minutes. The PDSC test conditions are given in Table 9. At the beginning of a PDSC run, the steel cell is pressurized with oxygen and heated at a rate of 40° C. per minute to the prescribed isothermal temperature. The induction time is measured from the time the sample reaches its isothermal temperature until the enthalpy change is observed. The longer the oxidation induction time, the better the oxidation stability of the oil.

TABLE 9

PDSC Test Conditions

| Test Parameters | Settings |
| --- | --- |
| Isothermal Temperature | 200° C. |
| $O_2$ Gas Pressure | 500 psi |
| $O_2$ Gas Flow Rate Through Cell | 100 ml/min. |
| Catalyst | 50 ppm of Iron |
| Sample Holder | Open Aluminum Pan |
| Sample size | 1.0-2.0 mg |
| Induction Time | Enthalpy Change |

All test blends were mechanically mixed for 15 minutes under a nitrogen atmosphere. For every 50 grams of test blend prepared, 40 μl of oil soluble ferric naphthenate (6 weight percent in mineral oil) was added, prior to PDSC testing, to facilitate 50 ppm of iron in oil. Each blend was tested twice under the PDSC conditions described in Table 9 at 200° C. The OIT results of the blends of Examples 10-12 and Comparative Example C are given in Table 10.

TABLE 10

| Ex./Comp. Ex. | PDSC Results Time, minutes |
|---|---|
| Example 10 | 17.7 |
| Example 11 | 17.2 |
| Example 12 | 16.0 |
| Comp. Ex. C | 4-5 |

It can be seen from the above data that the multigrade motor oil formulations containing the diaromatic amine derivative additives of the present invention exhibited significantly better oxidative stability than the multigrade motor oil formulations containing no antioxidant.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A diaromatic amine derivative having the general formula:

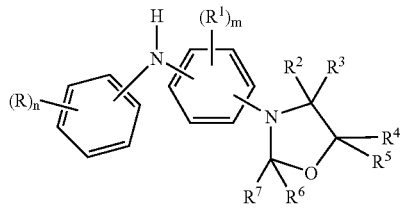

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing an ester group, an ether group, an aromatic group, or an amide group.

2. The diaromatic amine derivative of claim 1, wherein R, $R^1$, $R^3$, $R^4$, $R^6$, and $R^7$ are hydrogen.

3. The diaromatic amine derivative of claim 1, wherein R, $R^1$, $R^3$, $R^4$, $R^6$ and $R^7$ are hydrogen and $R^2$ and $R^5$ independently are a $C_1$-$C_{32}$ alkyl group optionally containing the ester group or the ether group.

4. The diaromatic amine derivative of claim 1, wherein R, $R^1$, $R^3$, $R^4$, $R^6$ and $R^7$ are hydrogen and $R^2$ and $R^5$ independently are a $C_1$-$C_{12}$ alkyl group optionally containing the ester group or the ether group.

5. The diaromatic amine derivative of claim 1, wherein two R groups together with the carbon atom to which they are bonded are joined together to form a saturated, unsaturated or partially saturated $C_3$-$C_{30}$ ring structure optionally containing one or more heterocyclic groups.

6. A reaction mixture comprising two or more of the diaromatic amine derivatives of claim 1.

7. A reaction mixture comprising two or more of the diaromatic amine derivatives of claim 2.

8. A reaction mixture comprising two or more of the diaromatic amine derivatives of claim 3.

9. A reaction mixture comprising two or more of the diaromatic amine derivatives of claim 4.

10. A reaction mixture comprising two or more of the diaromatic amine derivatives of claim 5.

11. A process for preparing one or more diaromatic amine derivatives having the general formula:

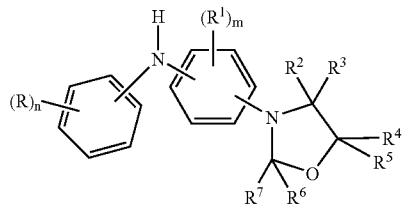

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing an ester group, an ether group, an aromatic group, or an amide group, the process comprising reacting a hydroxyl ethylene amine intermediate of the formula

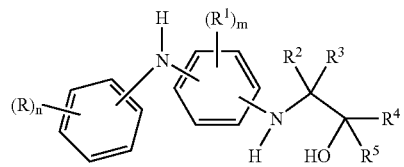

wherein n, m, R, $R^1$, $R^2$, $R^3$, $R^4$, and $R^5$ have the aforementioned meanings, with a ketone or aldehyde.

12. A process for preparing one or more diaromatic amine derivatives having the general formula:

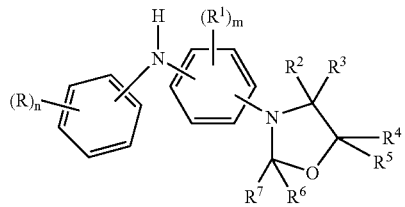

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing an ester group, an ether group, an aromatic group, or an amide group, the process comprising (a) reacting a substituted or unsubstituted N-phenyl-p-phenylenediamine derivative with an organic epoxide group; and (b) reacting the product of step (a) with a ketone or aldehyde.

13. The process of claim 12, wherein the substituted or unsubstituted N-phenyl-p-phenylenediamine derivative is represented by the formula:

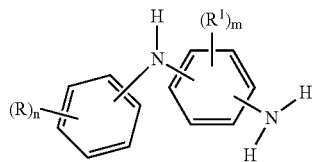

wherein n, m, R and $R^1$ have the aforementioned meanings.

14. The process of claim 12; wherein the substituted or unsubstituted N-phenyl-p-phenylenediamine derivative is selected from the group consisting of N-phenyl-p-phenylenediamine, N-phenyl-o-phenylenediamine, N-naphthyl-p-phenylenediamine, N-naphthyl-o-phenylenediamine, N-(5,6,7,8-tetrahydro-1-naphthyl)-p-phenylenediamine, N-(5,6,7,8-tetrahydro-2-naphthyl)-p-phenylenediamine, N-(5,6,7,8-tetrahydro-1-naphthyl)-o-phenylenediamine, N-(5,6,7,8-tetrahydro-2-naphthyl)-o-phenylenediamine, and combinations thereof.

15. The process of claim 12, wherein the organic epoxide group is selected from the group consisting of an epoxidized hydrocarbon olefin, epoxidized vinyl ether, epoxidized vegetable oil, epoxidized unsaturated fatty esters of a vegetable oil and mixtures thereof.

16. The process of claim 12, wherein the N-phenyl-p-phenylenediamine is N-p-phenylphenylenediamine and the organic epoxide group is selected from the group consisting of 1,2-epoxyalkyl, 1,2-epoxycycloalkyl and mixtures thereof.

17. The process of claim 12, wherein the N-phenyl-p-phenylenediamine and organic epoxide group are reacted in a mole ratio of about 0.9:1 to about 1:1 of organic epoxide group to N-phenyl-p-phenylenediamine.

18. The process of claim 12, wherein the ketone is selected from the group consisting of acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone, methyl sec butyl ketone, methyl tert-butyl ketone, ethyl butyl ketone, ethyl isobutyl ketone, ethyl sec-butyl ketone, ethyl tert-butyl ketone, propyl butyl ketone, isopropyl butyl ketone, propyl isobutyl ketone, propyl sec-butyl ketone, propyl tert butyl ketone, isopropyl isobutyl ketone, isopropyl sec-butyl ketone, isopropyl tert-butyl ketone, dibutyl ketone, diisobutyl ketone, di-sec-butyl ketone, di-tert-butyl ketone, butyl isobutyl ketone, butyl sec-butyl ketone, butyl tert-butyl ketone, isobutyl sec-butyl ketone, isobutyl tert-butyl ketone, sec-butyl tert-butyl ketone, 5-heptanone, 5-methyl-2-hexanone (methyl isoamyl ketone), 4-methyl-2-hexanone, 3-methyl-2-hexanone, 3,4-dimethyl-2-pentanone, 3,3-dimethyl-2-pentanone, 4,4-dimethyl-2-pentanone, 3-octanone, 4-methyl-3-heptanone, 5-methyl-3-heptanone, 6-methyl-3-heptanone, 4,4-dimethyl-3-hexanone, 4,5-dimethyl-3-hexanone, 5,5-dimethyl-3-hexanone, 4-nonanone, 5-methyl-4-octanone, 6-methyl-4-octanone, 7-methyl-4-octanone, 5,5-dimethyl-4-neptanone, 5,6-dimethyl-4-heptanone, 6,6-dimethyl-4-heptanone, 2-undecanone, cyclopropanone, cyclobutanone, cyclopentanone, cyclohexanone, cycloheptanone, cyclooctanone, cyclononanone, cyclodecanone, cycloundecanone, cyclododecanone and combinations thereof.

19. The process of claim 12, wherein the aldehyde is selected from the group consisting of formaldehyde, acetaldehyde, propionaldehyde, butyraldehyde, 2-methylpropionaldehyde, valeraldehyde, 2-methyl-butanal, caproaldehyde, hexyldehyde, heptaldehyde, octaldehyde, nonaldehyde, decaldehyde, undecaldehyde, dodecaldehyde, benzaldehyde, phenylacetaldehyde, and combinations thereof.

20. The process of claim 12, wherein the reaction of the substituted or unsubstituted N-phenyl-p-phenylenediamine derivative and the organic epoxide group is carried out in a suitable solvent and in the presence of an acid catalyst.

21. A lubricating oil composition comprising (a) at least one oil of lubricating viscosity and (b) an antioxidant improving effective amount of one or more diaromatic amine derivatives having the general formula:

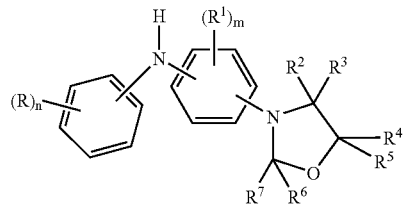

wherein n is from 0 to 5; m is from 0 to 4; each R substituent is independently hydrogen or a straight or branched $C_1$-$C_{32}$ alkyl group or alkenyl group or two R substituents together with the carbon atom to which they are bonded are joined together to form an unsaturated, partially saturated or saturated $C_3$-$C_{30}$ ring structure optionally containing one or more heteroatoms, each $R^1$ substituent is independently hydrogen or a straight or branched $C_1$-$C_{32}$ alkyl group or alkenyl group and $R^2$, $R^3$, $R^4$, $R^5$, $R^6$ and $R^7$ are independently hydrogen or a straight or branched $C_1$-$C_{32}$ alkyl group or alkenyl group optionally containing an ester group, an ether group, an aromatic group, or an amide group.

22. The lubricating oil composition of claim 21, wherein $R^1$, $R^3$, $R^4$, $R^6$, $R^7$ and R are hydrogen.

23. The lubricating oil composition of claim 21, wherein $R^1$, $R^3$, $R^4$, $R^6$, $R^7$ and R are hydrogen and $R^2$ and $R^5$ independently are a $C_1$-$C_{32}$ alkyl group optionally containing the ester group or the ether group.

24. The lubricating oil composition of claim 21, wherein $R^1$, $R^3$, $R^4$, $R^6$, $R^7$ and R are hydrogen and $R^2$ and $R^5$ independently are a $C_1$-$C_{12}$ alkyl group optionally containing the ester group or the ether group.

25. The lubricating oil composition of claim 21, wherein two R substituents together with the carbon atom to which they are bonded are joined together to form an unsaturated, partially saturated or saturated $C_3$-$C_{30}$ ring structure optionally containing one or more heteroatoms.

26. The lubricating oil composition of claim 21, wherein the at least one oil of lubricating viscosity is selected from the group consisting of engine oils, transmission fluids, hydraulic fluids, gear oils, marine cylinder oils, compressor oils, refrigeration lubricants and mixtures thereof.

27. The lubricating oil composition of claim 21, wherein the at least one oil of lubricating viscosity has a viscosity of about 1.5 to about 2000 centistokes (cSt) at 100° C.

28. The lubricating oil composition of claim 21, wherein the at least one oil of lubricating viscosity has a kinematic viscosity of about 1.5 cSt to about 30 cSt at 100° C.

29. The lubricating oil composition of claim 21, wherein the at least one oil of lubricating viscosity has a kinematic viscosity of about 1.5 cSt to about 16 cSt at 100° C.

30. The lubricating oil composition of claim 21, wherein the at least one oil of lubricating viscosity has a kinematic viscosity of about 1.5 cSt to about 12 cSt at 100° C.

31. The lubricating oil composition of claim 21, wherein the at least one oil of lubricating viscosity has a SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40.

32. The lubricating oil composition of claim 21, further comprising at least one lubricating oil additive selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

33. The lubricating oil composition of claim 21, further comprising at least one lubricating oil additive selected from the group consisting of an alkylated diphenylamine, hindered phenolic, substituted or unsubstituted phenylenediamine, oil soluble copper compound, sulfur containing compound known to impart oxidation stability and mixtures thereof.

34. The lubricating oil composition of claim 33, wherein the sulfur containing compound known to impart oxidation stability is selected from the group consisting of phenothiazines, sulfurized olefins, thiocarbamates, sulfur bearing hindered phenolic s, zinc dialkyldithiophosphates and mixtures thereof.

35. The lubricating oil composition of claim 21, comprising a mixture of two or more of the diaromatic amine derivatives.

36. The lubricating oil composition of claim 21, having a phosphorous content of less than about 0.1 weight percent.

37. The lubricating oil composition of claim 21, having a phosphorous content of less than about 0.08 weight percent.

38. The lubricating oil composition of claim 21, having a phosphorous content of less than about 0.05 weight percent.

39. An additive package comprising about 1 to about 75 weight percent of one or more of the diaromatic amine derivative of claim 1.

40. An additive package comprising about 1 to about 75 weight percent of a reaction mixture comprising two or more of the diaromatic amine derivatives of claim 1.

41. A stabilizer-containing composition comprising (a) an organic material subject to oxidative, thermal, and/or light-induced degradation and in need of stabilization to prevent or inhibit such degradation; and (b) a stabilization effective amount of one or more diaromatic amine derivatives of claim 1.

42. The stabilizer-containing composition of claim 41, wherein the organic material is selected from the group consisting of compounded tires, polyols, plastics, urethanes, greases, motor oils, rubber belts, cables, gaskets, seals and rubber products in the garment and carpet industries.

43. A method for stabilizing an organic material subject to oxidative, thermal, and/or light-induced degradation and in need of stabilization to prevent or inhibit such degradation, the method comprising adding to the organic material a stabilizing amount of one or more diaromatic amine derivatives of claim 1.

44. The method of claim 43, wherein the organic material is selected from the group consisting of compounded tires, polyols, plastics, urethanes, greases, motor oils, rubber belts, cables, gaskets, seals and rubber products in the garment and carpet industries.

\* \* \* \* \*